United States Patent
Stamler (12)

(10) Patent No.: US 6,676,855 B2
(45) Date of Patent: Jan. 13, 2004

(54) USE OF A BLOOD-FLOW DECREASE PREVENTING AGENT IN CONJUNCTION WITH INSUFFLATING GAS

(75) Inventor: Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 33 days.

(21) Appl. No.: 09/919,931

(22) Filed: Aug. 2, 2001

(65) Prior Publication Data

US 2003/0032917 A1 Feb. 13, 2003

(51) Int. Cl.$^7$ .............................................. A61K 33/00
(52) U.S. Cl. ........................................................ 252/372
(58) Field of Search ........................... 252/372; 424/718, 424/700

(56) References Cited

U.S. PATENT DOCUMENTS

| 4,048,992 | A | | 9/1977 | Lindemann et al. ......... 128/184 |
| 5,412,147 | A | * | 5/1995 | Landscheidt et al. ....... 558/488 |
| 5,427,797 | A | * | 6/1995 | Frostell et al. ............... 424/434 |
| 5,489,610 | A | * | 2/1996 | Fung et al. ................... 514/506 |
| 5,670,177 | A | * | 9/1997 | Briend et al. ................. 424/718 |
| 5,823,180 | A | | 10/1998 | Zapol ..................... 128/200.24 |
| 6,314,956 | B1 | | 11/2001 | Stamler et al. ......... 128/200.24 |
| 6,440,393 | B1 | * | 8/2002 | Waldrep et al. ................ 424/45 |

FOREIGN PATENT DOCUMENTS

WO    WO 01/17596    3/2001

OTHER PUBLICATIONS

The Merck Manual of Diagnosis and Therapy, 16th edition, pp. 742–743 (1992).

* cited by examiner

Primary Examiner—Stanley S. Silverman
Assistant Examiner—Maribel Medina

(57) ABSTRACT

A blood-flow decrease preventing agent is used to negate or reduce the decreased oxygen delivery in abdominal organs caused by insufflating gas. Preferably a gas is delivered into the abdominal cavity consisting essentially of the insufflating gas and the blood-flow decrease preventing agent. Very preferably, a gas is used consisting essentially of carbon dioxide as the insufflating gas and ethyl nitrite as the blood-flow to abdominal organ decrease preventing agent.

7 Claims, 3 Drawing Sheets

USE OF A BLOOD-FLOW DECREASE PREVENTING AGENT IN CONJUNCTION WITH INSUFFLATING GAS

TECHNICAL FIELD

This invention is directed at negating or reducing decrease in blood-flow to abdominal organs which would otherwise have decreased oxygen delivery because of being contacted with an insufflating gas, typically carbon dioxide.

BACKGROUND OF THE INVENTION

In laparoscopic surgery or diagnosis, the insufflating gas used normally is carbon dioxide. However, the carbon dioxide pneumoperitoneum decreases blood-flow to abdominal organs, and this can result in elevated liver functions, decreased renal perfusion, hypercapneic acidosis (due to failure to remove acid from tissue because of abnormal blood-flow), and in the case of the pregnant female, impairment of blood-flow to fetus and severe hypoxemia in fetus.

SUMMARY OF THE INVENTION

One embodiment herein, denoted the first embodiment, is directed to a method for negating or reducing decrease in blood-flow and/or hypoxemia in an abdominal organ which would otherwise have decreased oxygen delivery because of decreased blood-flow therein because of insufflating gas being delivered into the abdominal cavity, comprising contacting said abdominal organ with a blood-flow to abdominal organ decrease preventing agent in a therapeutically effective amount, preferably comprising delivering the blood-flow to abdominal organ decrease preventing agent into the abdominal cavity as part of a gas consisting essentially of the blood-flow to abdominal organ decrease preventing agent in a therapeutically effective amount and an insufflating gas. The blood-flow to abdominal organ decrease preventing agent is preferably ethyl nitrite. The insufflating gas is a blood-flow decrease and hypoxemia causing insufflating gas and is typically carbon dioxide. Very preferably, the gas consisting essentially of blood-flow to abdominal organ decrease preventing agent and insufflating gas contains from 1 to 1,000 ppm ethyl nitrite, e.g., 50 to 200 ppm ethyl nitrite. Gas insufflation into the peritoneum also impairs fetal blood flow and ethyl nitrite or other vasoditating gas can diffuse into the blood to improve fetal blood flow and hypoxemia.

Pneumoperitoneum also impairs pulmonary function and raises blood pressure and ethyl nitrite has been shown to improve pulmonary function and can lower blood pressure.

The invention of the first embodiment involves a way to prevent or reverse with a drug a complication of a laparoscopic procedure and is analogous to giving a patient a drug to raise blood pressure if blood pressure drops during surgery. The invention of the first embodiment treats a complication of laparoscopic surgery or diagnosis.

The invention of the first embodiment involves the treatment of mammals, including humans.

Another embodiment herein, denoted the second embodiment, is directed to a gas consisting essentially of insufflating gas and a blood-flow to abdominal organ decrease preventing agent in a therapeutically effective amount, e.g., ethyl nitrite used in amount of 1 to 1,000 ppm, e.g., 50 to 200 ppm.

The term "abdominal organ" is used herein to mean an organ in the abdominal cavity or retroperitoneum or a fetus or placenta.

BRIEF DESCRIPTION OF THE DRAWINGS

In FIG. 3, CO2 means $CO_2$ and E—NO means ethyl nitrite.

DETAILED DESCRIPTION

Figure 1:
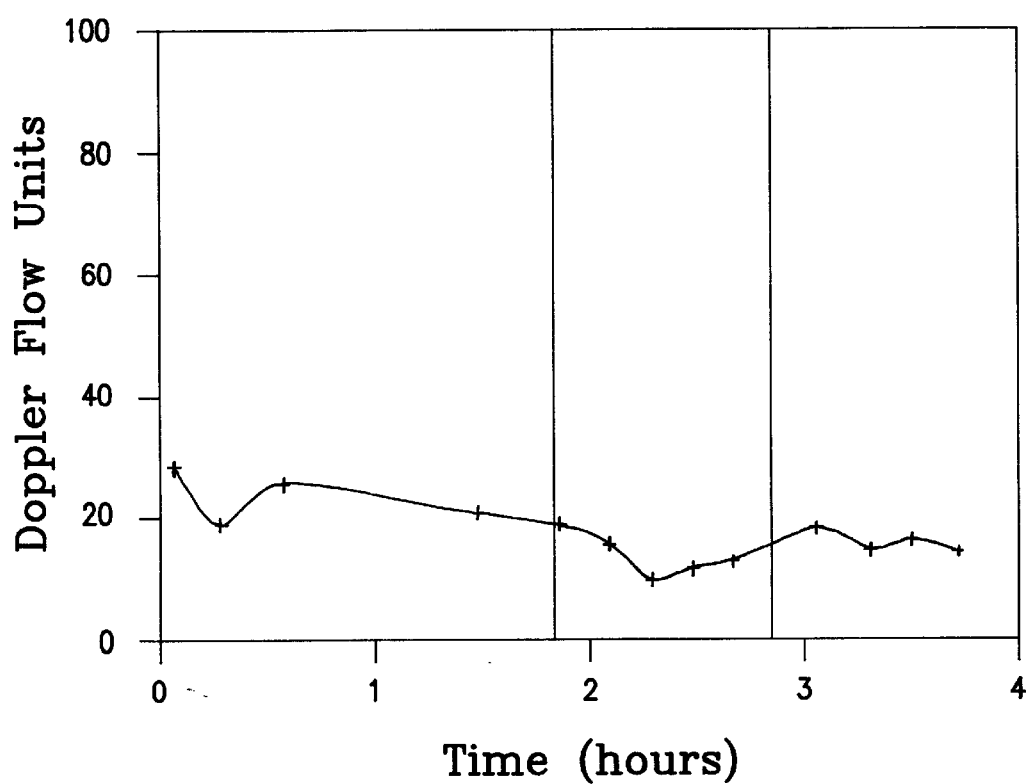
FIG. 1 is a graph of Time (hours) versus Doppler Flow Units and shows results for effect on liver in respect to blood-flow in liver, of carbon dioxide gas insufflation (15 mm Hg for 1 hour) as determined in the experiment of Example I and represents the current state-of-the-art.

We turn now to the embodiment herein, denoted the first embodiment herein, which is directed to a method for negating or reducing decrease in blood-flow and/or hypoxemia in an abdominal organ which would otherwise have decreased oxygen delivery because of decreased blood-flow therein because of carbon dioxide or other insufflating gas, e.g., helium, argon or nitrogen, being delivered into the abdominal cavity, comprising contacting said abdominal organ with a blood-flow to abdominal organ decrease preventing agent in a therapeutically effective amount.

The method is directed to use of a composition of matter in laparoscopic surgery or in a laparoscopic diagnostic procedure, as a therapeutic agent.

Laparoscopic surgery allows surgery with minimal tissue injury and relies on a miniature video camera and surgical instruments inserted into the abdominal cavity usually through a small cut in the umbilicus. After an initial cut, a needle adapted to deliver insufflating gas is inserted. Then the insufflating gas is delivered into the abdominal cavity to expand the abdominal cavity to enable better visualization and greater workspace. The pressure resulting from the gas delivery normally should not exceed 15 mm Hg. The insufflating gas conventionally consists of carbon dioxide. After sufficient expansion is obtained, a trocar is inserted through the umbilical cut. This is used for access to insert the miniature video camera and surgical instruments. The video camera provides high resolution visualization and allows proper manipulation of the surgical instruments to carry out surgery effectively.

Diagnostic laparoscopy corresponds to laparoscopic surgery so far as initial cut and insertion of insufflating gas is concerned but the video camera is inserted to obtain diagnosis and surgery is not carried out.

Some texts available from Amazon.com in June, 2001 on laparoscopy include the following: Ballantyne, G. H., Atlas of Laparoscopic Surgery; Eubanks, S. (ed), et al., Mastery of Endoscopic and Laparoscopic Surgery; Pappas, T. N., Atlas of Laparoscopic Surgery; Beshoff, J. T., et al., Atlas of Laparoscopic Retroperitoneal Surgery; MacIntyre, I. M. C., Practical Laparoscopic Surgery for General Surgeons (August 1994). The whole of each of these is incorporated herein by reference.

Surgery and diagnosis can be effected on abdominal organs within the peritoneum, e.g., on liver, or on opening of the peritoneum on retroperitoneal organs, e.g., kidneys and pancreas.

When the abdominal organs that are the subject of the laparoscopic procedure, are within the peritoneum, e.g., liver, then organs within the peritoneum would otherwise have decreased blood-flow and are beneficially acted by the invention herein. When the abdominal organs that are the subject of the laparoscopic procedure are retroperitoneal, then the retroperitoneal organs would otherwise have decreased blood-flow and serum creatine increases associated with kidney dysfunction and are beneficially aided by the invention herein.

The application of the first embodiment of the instant invention to laparoscopic surgery can be described as follows: In a method of laparoscopic surgery wherein an insufflating gas is delivered into the abdominal cavity to enable better visualization and greater work space, the step is carried out of contacting the abdominal organs contacted with the insufflating gas, with a blood-flow to abdominal organ decrease preventing agent in an effective amount.

The application of the first embodiment of the instant invention to a laparoscopic diagnostic procedure can be described as follows: In a method for laparoscopic diagnosis wherein an insufflating gas is delivered into the abdominal cavity to enable better visualization, the step is carried out of contacting the abdominal organs contacted with the insufflating gas, with a blood-flow to abdominal organ decrease preventing agent in an effective amount.

The blood-flow to abdominal organ decrease preventing agents include agents that cause blood vessel dilation or that increase blood-flow by decreasing platelets or by decreasing neutrophil or red blood plugging of vessels or by decreasing blood viscosity.

We turn now to the case of the first embodiment where the blood-decrease preventing agent is caused to contact abdominal organs by delivering the blood-flow to abdominal organ decrease preventing agent into the abdominal cavity as part of a gas consisting essentially of the blood-flow to abdominal organ decrease preventing agent in effective amount and an insufflating gas.

We turn now to use of the gas. As in the case of conventional laparoscopy, the pressure resulting from gas delivery should normally not exceed 15 mm Hg. Within this framework, the amount of gas should be sufficient to allow sufficient visualization and work space for laparoscopy.

The gas can be delivered using a $CO_2$ insufflator equipped with a pressure regulator.

As indicated above, the gas consists essentially of a blood-flow to abdominal organ decrease preventing agent in effective amount and the insufflating gas.

We turn now to the blood-flow to abdominal decrease preventing agent. The decrease in blood-flow referred to as being prevented is that which would, except for the invention here, be caused by the insufflating gas.

When the blood-flow to abdominal organ decrease preventing agent is administered as part of a gas, it must normally be a gas under the conditions of administration or must be converted to a gas for administration. The agents should not have a boiling point such that the temperature required to maintain them as gases in diluted form, i.e., in combination with insufflating gas, would harm an abdominal organ and preferably should not condense in the abdominal cavity.

The blood-flow to abdominal organ decrease preventing agents which are administered as part of a gas preferably have the formula $RX-NO_y$, where R is either not present or is hydrogen/proton or $C_1-C_7$-alkyl and X is oxygen, sulfur, nitrogen or metal selected, for example, from the group consisting of iron, copper, ruthenium and cobalt atoms or an alkyl or alkenyl or alkylthio or alkenylthio group containing from 1 to 7, e.g., 1 to 6, carbon atoms which is straight chain or branched, or $CF_3-$ or $CF_3S-$, and y is 1 or 2, excluding nitrous oxide. Specific treating agents of the $RX-NO_y$ class include, for example, ethyl nitrite (which is the very preferred blood-flow to abdominal organ decrease preventing agent for use in the embodiments herein and is used in examples herein), methyl nitrite, tert-butyl nitrite, isoamyl nitrite, trifluoronitrosomethane ($CF_3NO$), $CF_3SNO$, $CH_3SNO$, $CH_2=CHSNO$, $CH_2=CHCH_2SNO$, $ONSCH_2-CH_2-CH_2SNO$ and $CH_3CH_2CH_2SNO$. Alkyl nitrites can be prepared as described in Landsscheidt et al. U.S. Pat. No. 5,412,147. Ethyl nitrite is available commercially, e.g., diluted in ethanol. $CF_3NO$ is a commercial product or can be made by treatment of $CF_3I$ with $NO^-$ as described in J. Phys. Chem. 100, 10641 (1996). Aliphatic thionitrites, i.e., compounds of the form RSNO where R describes an alkyl or alkenyl or hydrogen moiety, can be prepared by treatment of the corresponding thiol with a source of $NO^+$ including, but not limited to, one or more of the following: tert-butyl nitrite, ethyl nitrite, nitrosonium tetrafluoborate ($NOBF_4$), nitrosonium perchlorate ($NOClO_4$), nitrosonium hydrogen sulfate ($NOHSO_4$), nitrosonium hydrogen phosphate ($NOH_2PO_4$), or HCl-acidified solutions of sodium nitrite.

Other blood-flow to abdominal organ decrease preventing agents for use in the embodiments herein, which are normally gases or which can be converted into a gas for administration, include NOQ or QNO where Q is halogen, e.g., Cl, Br or F, or hydrogen or NOQ or QNO generating agents, alkyl nitrososulfinates ($RSO_2NO$) where the alkyl group contains from 1 to 10 carbon atoms, thionitrosochloronitrite (SOClONO), thionyldinitrite ($SO(ONO)_2$) and alkyl (including small peptides) thionitrites ($RSNO_2$) wherein the alkyl group contains from 1 to 10 carbon atoms or is small peptide, and nitrosourea.

Other blood-flow to abdominal organ decrease preventing agents for use in the embodiments herein, which are normally gases, are nitric oxide (NO), $NO_2$ and $N_2O_3$.

Still another blood-flow to abdominal organ decrease preventing agent for use in the embodiments herein, which is normally a gas, is carbon monoxide.

We turn now to cases of the first embodiment where the blood-flow to abdominal organ decrease preventing agent is not administered as part of a gas.

The blood-flow to abdominal organ decrease preventing agents can be a administered as a dry powder or as a solution which is applied topically or nebulized on to an abdominal organ, such as a solution of an NO donor (an NO donor donates nitric oxide or a related species and more generally provides nitric oxide bioactivity, that is activity which is identified wit nitric oxide, e.g., vasolidation) such as a nitrosothiol or nitroglycerin or a calcium channel blocker such as verapamil. Suitable NO donors are described in "Methods in Nitric Oxide Research," edited by Feelisch, M., and Stamler, J. S., John Wiley & Sons, New York, 1996, at pages 71–115 and in Zapol U.S. Pat. No. 5,823,180 and in WO 01/17596 published Mar. 15, 2001. Other blood-flow to abdominal organ decrease providing agents which can be administered in solutions include prostaglandins $E_1$ and I. Other blood-flow to abdominal organ decrease preventing agents which can be administered in solution or nebulized are angiotensin enzyme inhibitors, e.g., captepril.

As indicated above, the blood-flow to abdominal organ decrease preventing agent for use in the embodiments herein is used in a therapeutically effective amount. This is an amount that negates or reduces the blood-flow to abdominal organ decrease and relieves or reduces the resulting hypoxemia that without the instant invention would occur, to extent of effecting blood-flow that is at least 5% of that present in the organ if it were not contacted with insufflating agent, typically carbon dioxide, as measured by Doppler or tissue oxygenation.

In the embodiment where the blood-flow to abdominal organ decrease preventing agent is administered as pant of a gas, it typically constitutes from 1 to 1,000 ppm, e.g., 50 to 200 ppm, of the gas consisting essentially of insufflating gas, typically carbon dioxide, and blood-flow to abdominal organ decrease preventing agent.

The blood-flow to abdominal organ decrease preventing agent can be admixed with carbon dioxide or other insufflating gas to provide a gas for administration, e.g., by conventional gas blending methods.

Where the blood-flow to abdominal organ decrease preventing agent is administered as a dry powder or as a solution, it can be administered in an amount which maintains patient's blood-flow to at least 5% of that present in the abdominal organ before contact with insufflating gas as measured by Doppler or tissue oxgenation.

We turn now to the second embodiment herein, i.e., the gas consisting essentially of insufflating gas, typically carbon dioxide, and a blood-flow to abdominal organ decrease preventing agent in a therapeutically effective amount. The blood-flow to abdominal organ decrease preventing agents are those described above in conjunction with the first embodiment herein. The effective amount is that described above in conjunction wit the first embodiment herein. Very preferably, the gas consists essentially of carbon dioxide and from 1 to 1,000 ppm, e.g., 50 to 200 ppm, blood-flow to abdominal organ decrease preventing agent, very preferably ethyl nitrite. Admixture of the carbon dioxide and blood-flow to abdominal organ decrease preventing agent, can be effected as described for the first embodiment.

The invention herein supported by or illustrated by the following working examples.

EXAMPLE I

Figure 2:
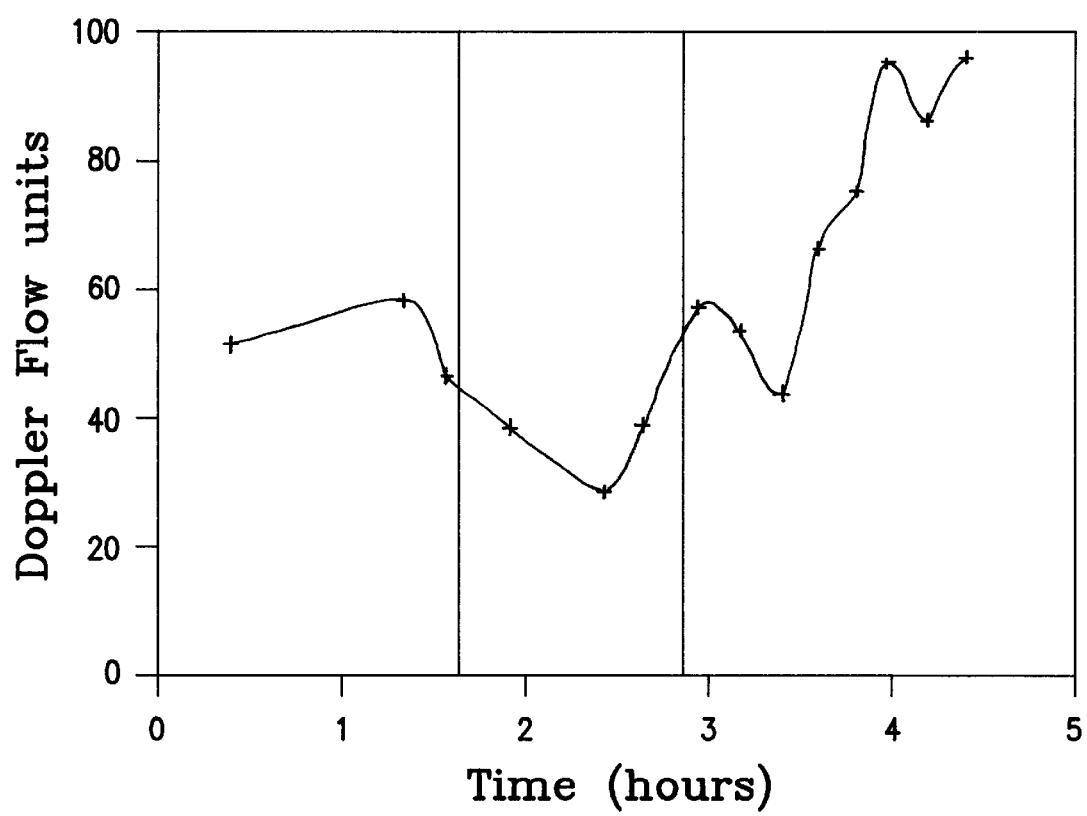
FIG. 2 is a graph of Time (hours) versus Doppler Flow Units and shows results for effect on liver in respect to blood-flow in liver, of insufflation with carbon dioxide gas containing 100 ppm ethyl nitrite as determined in the experiment of Example I and represents the invention.
Figure 3:
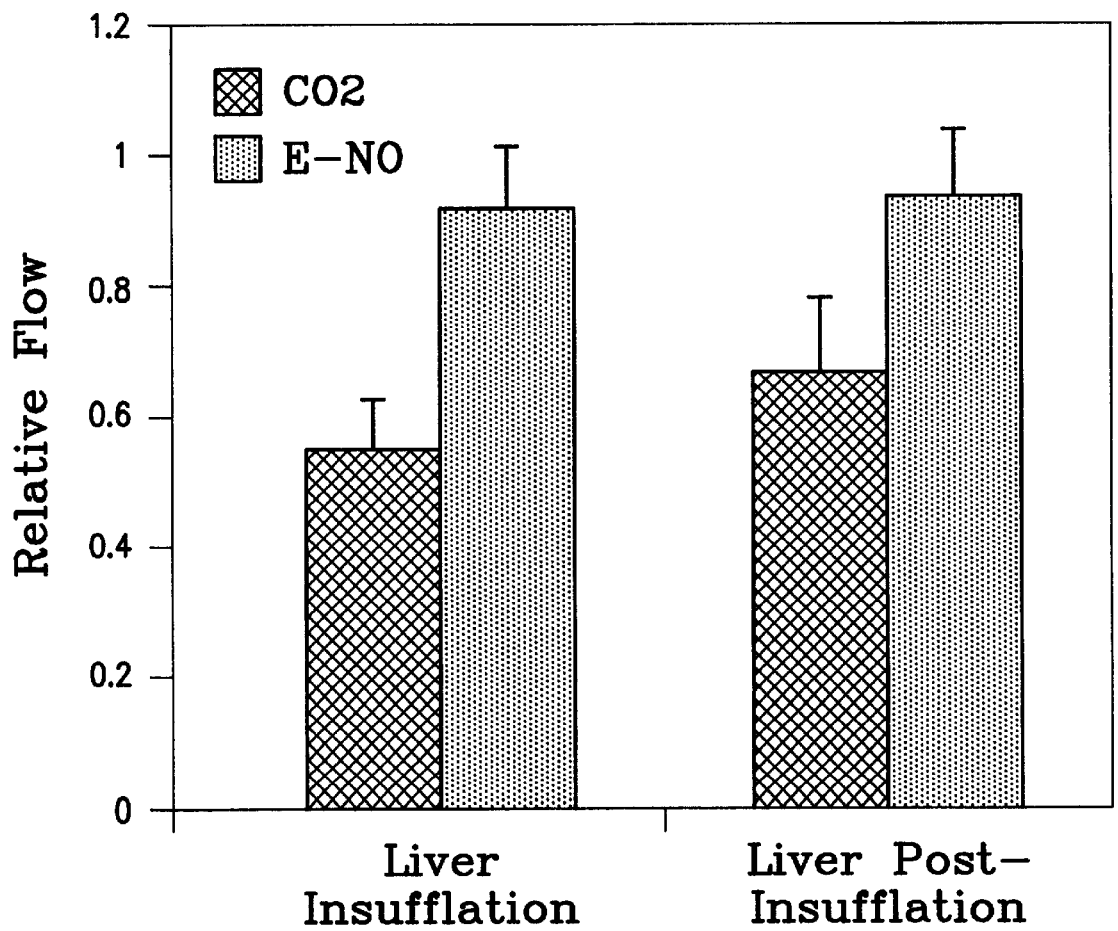
FIG. 3 depicts graphs of relative blood-flow compared to baseline and shows effect on liver of carbon dioxide alone and of gas consisting of carbon dioxide and 100 ppm ethyl nitrite and shows results during insufflation and two hours post insufflation as determined in the experiment of Example I.

Ten adult pigs were anesthetized at time zero using halothane anesthetic. A small cut was made in the abdomen to allow access inside the peritoneum. In the case of one group of five pigs, denoted group A, an insufflating needle was inserted, and starting at time 1 hour and 48 minutes, an insufflating gas consisting of carbon dioxide was delivered into the abdominal cavity to standard operating pressure (of 15 mm Hg) and the insufflating gas was maintained in the abdominal cavity for 1 hour whereupon the insufflating gas was removed by suction. In the case of another group of five pigs, denoted group B, an insufflating needle was inserted, and starting at time 1 hour and 35 minutes, an insufflating gas consisting of carbon dioxide and 100 ppm ethyl nitrite was delivered to the abdominal cavity to standard operating pressure and the insufflating gas was maintained in the abdominal cavity for about 1⅕ hour whereupon the insufflating gas was removed by suction. In both cases, blood-flow in liver was monitored by a laser Doppler flow method (a standard method where ultrasonic waves are projected at flowing blood and bounce back) whereby blood-flow is determined starting at time 5 minutes after time zero in the case of group A, and starting at about time 20 minutes after time zero in the case of group B and continuing until 2 hours after insufflating gas was removed. Results are shown in FIGS. 1–3. In FIGS. 1 and 2, the Doppler Flow Units are arbitrary units. In FIG. 3, the term "Relative Flow" means relative blood-flow in liver compared to baseline. FIG. 1 shows blood-flow results (flow in liver) for group A (carbon dioxide only). FIG. 1 illustrates that carbon dioxide pneumoperitoneum produces a decrease in blood-flow to the liver, which was sustained even after the procedure was completed. FIG. 2 shows blood-flow results (flow in liver) for group B (carbon dioxide together with 100 ppm ethyl nitrite). FIG. 2 shows that ethyl nitrite protects against carbon dioxide induced decline in liver perfusion. FIG. 3 shows average values of blood-flow in liver for "Liver Insufflation" that is while insufflating gas is present, and "Liver Post-Insufflation," that is 2 hours after insufflating gas is removed. FIG. 3 shows about 70% more blood-flow in the ethyl nitrite case during insufflation and about 40% more blood-flow in the ethyl nitrite case 2 hours post-insufflation. The same protection by ethyl nitrite against renal dysfunction is predicted where the peritoneum is opened.

EXAMPLE II

A 23-year-old black female, 32 weeks pregnant, undergoes laparoscopic evaluation for right lower quadrant pain. Thirty minutes into the procedure, fetal $PO_2$, measured by an electrode placed on the head, is 7 mm Hg. 100 ppm ethyl nitrite is added to the carbon dioxide insufflating gas, and the fetal $PO_2$ increases to 25 mm Hg.

EXAMPLE III

A 70-year-old male undergoes laparoscopic cholecystectomy. One hour into the procedure, liver function tests start to rise and the patient complains of abdominal pain suggestive of intestinal ischemia. Ethyl nitrite 100 ppm is added to the insufflating gas with resolution of abdominal pain.

EXAMPLE IV

A 55-year-old woman with renal artery stenosis undergoes laparoscopy appendectomy and diagnostic evaluation of a renal mass. Because of concerns regarding decreased renal perfusion, 100 ppm ethyl nitrite is added to insufflating gas and protects against decrease a blood-flow.

EXAMPLE V

A sixty-year-old white female undergoes laparoscopic appendectomy. Because of concerns of impaired renal function, pulmonary function and hypertension, nitroglycerin (3 cc of 100 micromolar) is nebulized into the abdominal cavity. Blood pressure increases are prevented and pulmonary and renal functions are kept stable.

Variations

Variations of the above will be obvious to those skilled in the art. Thus, the scope of the invention is defined by the claims.

What is claimed is:

1. A gas consisting essentially of an insufflating gas comprising carbon dioxide and a blood-flow to abdominal organ decrease preventing agent in a therapeutically effective amount ranging from 1 to 1,000 ppm; with the proviso that the blood-flow to abdominal organ decrease preventing agent is not nitric oxide.

2. The gas of claim 1, where the blood-flow to abdominal organ decrease preventing agent is selected from the group consisting of gases having the formula $RX—NO_y$ where R is either not present or is hydrogen or proton or $C_1$–$C_7$-alkyl, X is oxygen, sulfur, nitrogen or metal selected from the group consisting of iron, copper, ruthenium and cobalt atoms or an alkyl or alkenyl or alkylthio or alkenylthio group, containing from 1 to 7 carbon atoms, and y is 1 or 2 provided that RX—$NO_y$ is not nitrous oxide.

3. The gas of claim 2, where the blood-flow to abdominal organ decrease preventing agent is an alkyl nitrite.

4. The gas of claim 3, where the alkyl nitrite is ethyl nitrite.

5. The gas of claim 1, where the blood-flow to abdominal organ decrease preventing agent is selected from the group consisting of gases having the formula NOQ or QNO where Q is halogen or hydrogen, NOQ or QNO generating agents, alkyl nitrososulfinates where the alkyl group contains from 1 to 10 carbon atoms, thionitrosochioronitrite, thionyldinitrite, $RSNO_2$ where R is an alkyl group containing from 1 to 10 carbon atoms or is a small peptide, nitrosourea, $NO_2$, $N_2O_3$ and carbon monoxide.

6. A gas consisting essentially of insufflating gas which is carbon dioxide and a blood-flow to abdominal organ decrease preventing agent in a therapeutically effective amount ranging from 1 to 1,000 ppm, the blood-flow to abdominal organ decrease preventing agent being ethyl nitrite.

7. The gas of claim 6, containing 50 to 200 ppm ethyl nitrite.

* * * * *

UNITED STATES PATENT AND TRADEMARK OFFICE
CERTIFICATE OF CORRECTION

PATENT NO. : 6,676,855 B2  Page 1 of 1
DATED : January 13, 2004
INVENTOR(S) : Jonathan S. Stamler It is certified that error appears in the above-identified patent and that said Letters Patent is hereby corrected as shown below:

Column 8,
Line 1, "thionitrosochioronitrite" should be -- thionitrosochloronitrite --.

Signed and Sealed this

Thirtieth Day of March, 2004

JON W. DUDAS
*Acting Director of the United States Patent and Trademark Office*